US008822166B2

(12) United States Patent
Alkon et al.

(10) Patent No.: US 8,822,166 B2
(45) Date of Patent: Sep. 2, 2014

(54) STIMULUS-ELICITED GENOMIC PROFILE MARKERS OF ALZHEIMER'S DISEASE

(75) Inventors: Daniel L. Alkon, Bethesda, MD (US); Tapan Kumar Khan, Morgantown, WV (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 627 days.

(21) Appl. No.: 12/510,707

(22) Filed: Jul. 28, 2009

(65) Prior Publication Data

US 2010/0021913 A1 Jan. 28, 2010

Related U.S. Application Data

(60) Provisional application No. 61/084,154, filed on Jul. 28, 2008.

(51) Int. Cl.
*G01N 33/567* (2006.01)
*G01N 33/561* (2006.01)

(52) U.S. Cl.
USPC ............. 435/7.21; 424/9.1; 435/7.9; 435/378

(58) Field of Classification Search
None
See application file for complete search history.

(56) References Cited

U.S. PATENT DOCUMENTS

| | | | |
|---|---|---|---|
| 5,242,932 | A | 9/1993 | Gandy et al. |
| 5,385,915 | A | 1/1995 | Buxbaum et al. |
| 6,077,686 | A | 6/2000 | Der et al. |
| 6,080,582 | A | 6/2000 | Alkon et al. |
| 6,080,784 | A | 6/2000 | Driedger et al. |
| 6,107,050 | A | 8/2000 | Alkon et al. |
| 7,595,167 | B2 | 9/2009 | Khan et al. |
| 2001/0051344 | A1 | 12/2001 | Shalon et al. |
| 2003/0108956 | A1 | 6/2003 | Alkon et al. |
| 2003/0153014 | A1 | 8/2003 | Shen et al. |
| 2004/0014678 | A1 | 1/2004 | Favit et al. |
| 2004/0086905 | A1 | 5/2004 | Das et al. |
| 2005/0059092 | A1 | 3/2005 | Zhao et al. |
| 2005/0075393 | A1 | 4/2005 | Nishizaki et al. |
| 2007/0082366 | A1 | 4/2007 | Khan et al. |
| 2009/0029873 | A1 | 1/2009 | Khan et al. |

FOREIGN PATENT DOCUMENTS

| | | |
|---|---|---|
| EP | 0 735 370 A | 10/1996 |
| JP | 06-279311 | 10/1994 |
| JP | 10-090263 A | 4/1998 |
| WO | WO 93/11231 A | 6/1993 |
| WO | WO 00/20867 A | 4/2000 |
| WO | WO 00/70099 | 11/2000 |
| WO | WO 01/69244 A2 | 9/2001 |
| WO | WO 02/10768 A2 | 2/2002 |
| WO | WO 02/50013 A1 | 6/2002 |
| WO | WO 02/067764 | 9/2002 |
| WO | WO02/067764 * | 9/2002 |
| WO | WO 03/102016 A2 | 12/2003 |
| WO | WO 2004/083241 A2 | 9/2004 |
| WO | 2006050475 | 5/2006 |
| WO | 2006054979 | 5/2006 |
| WO | WO 2007/043998 | 4/2007 |
| WO | WO 2007/044094 A1 | 4/2007 |
| WO | WO 2007/047029 | 4/2007 |
| WO | WO 2007/149985 A2 | 12/2007 |
| WO | WO 2008/100449 | 8/2008 |
| WO | WO2008/148115 A1 * | 12/2008 |
| WO | WO 2008/148115 A1 | 12/2008 |

OTHER PUBLICATIONS

Pasinetti GM., J Neurosci Res., 65(6):471-476, Aug. 31, 2001.*
Johnson et al., Cellular Signalling, 21:1471-1478, 2009.*
Shaw et al., Nature Reviews, 6:295-303, 2007.*
Weeraratna et al., Experimental Cell Research, 313:450-461, 2007.*
Shaw et al., Nature Reviews Drug Discovery, 6:296-303, Apr. 2007.*
Brooks, et al., "Gene expression profiles of metabolic enzyme transcripts in Alzheimer's disease", Brain Res. 2007; 1127(1): 127-35.
Dunckley, et al., "Gene expression correlates of neurofibrillary tangles in Alzheimer's disease", Neurobiol Aging 2006; 27(10): 1359-1371.
Liang, et al., "Altered neuronal gene expression in brain regions differentially affected by Alzheimer's disease: a reference data chart", Physiol Genomics 2008; 33: 240-256.
Loring, et al., "A Gene Expression Profile of Alzheimer's Disease", DNA and Cell Biology, 2001; 20(11): 683-695.
Nagasaka, et al., "A unique gene expression signature discriminates familial Alzheimer's disease mutation carriers from their wild-type siblings", Proc. Natl. Acad. Sci. USA 2005; 102(41): 14854-14859.
Gebreyesus, K, et al., "Bradykinin elevates tyrosine hydroxylase and dopamine beta-hydroxylase mRNA levels in PC12 cells," Brain Research (1993), 345-348, vol. 608(2).
Ning, et al., "Early response gene signalling in bryostatin-stimulated primary B chronic lymphocytic leukaemia cells in vitro," Biochemical Journal (1996), 59-65, vol. 319(1).
Zhao, et al., "Map Kinase Signaling cascade dysfunction specific to alzheimer's disease in fibroblasts," Neurobiology of Disease (2002), 166-183, vol. 11(1).
International Search Report dated Nov. 4, 2009, PCT/US2009/051931.
Alkon et al., Protein Synthesis Required for Long-Term Memory is Induced by PKC Activation on Days Before Associative Learning, Proc. Natl. Acad. Sci. USA,102:16432-16437 (2005).
Anderson et al., "Oxidative Signalling and Inflammatory Pathways in Alzheimer's Disease," Biochem. Soc. Symp., 67:141-149 (2001).
Arendt et al., "Increased Expression and Subcellular Translocation of the Mitogen Activated Protein Kinase Kinase and Mitogen-Activated Protein Kinase in Alzheimer's Disease," Neuroscience, 68(1):5-18 (1995).

(Continued)

*Primary Examiner* — Daniel E Kolker
*Assistant Examiner* — Stacey N MacFarlane
(74) *Attorney, Agent, or Firm* — Finnegan, Henderson, Farabow, Garrett & Dunner LLP

(57) ABSTRACT

The present invention relates to a method for diagnosing Alzheimer's Disease (AD) using PKC-elicited gene expression profiles. PKC-activation elicits different genomic profiles in AD cells, as compared with control cells, which can be used to diagnose AD and individuals at risk for developing AD.

12 Claims, 2 Drawing Sheets

(56) References Cited

OTHER PUBLICATIONS

Balin et al., "Normal replicative lifespan of Alzheimer skin fibroblasts", Neurobiol Aging, vol. 9, pp. 195-198 (1988).
Baker et al., "System Manifestation of Alzheimer's Disease," Age, 11:60-65 (1988).
Barrow et al., "Functional Phenotype in Transgenic Mice Expressing Mutant Human Presenilin-1," Nuerogiology of Disease 7, 119-126 (2000).
Bassa BV, et al., "Lysophosphatidylcholine Activates Mesangial Cell PKKC and MAP Kinase by PLCy-land Tyrosine Kinase-Ras Pathways," Am J Physiol, 277:F328-2337 (1999).
Becton, Dickenson& Co., BD GentestTM Primary Hepatocytes, 13 (2008).
Bernier et al., "Bradykinin-regulated Interactions of the Mitogen-activated Protein Kinase Pathway with the Endothelial Nitric-oxide Synthase," J. Biol. Chem., 275:30707-30715 (2000).
Berridge, "Inositol Triphosphate and Diacylglycerol as Second Messengers," Biochem J., 220:345-360 (1984).
Biernat et al., "Phosphorylation of Ser 262 Strongly Reduces Binding of Tau to Microtubules: Distinction beteen PHF-like Immunoreactivity and Microtubule Binding," Neuron, 11:153-163 (1993).
Blanchard et al., "Hyperphosphorylation of Human TAU by Brain Kinase PK40et beyond Phosphorylation 12 by cAMP-dependent PKA: Relation to Alzheimer's Disease." Biochem. Biophys. Res. Commun., 200(1):187-194 (1994).
Bockman et al., "Kinins and Kinin Receptors; Importance for the Activation of Leukocytes," Journal of Leukocyte Biology, 68 (Nov. 2000).
Bondy et al., "The PHA-Induced Calcium Signal in Lymphocytes is Altered After Blockade of K+-Channels in Alzheimer's Disease," J. Psychiat. Res., 30(3):217-227 (1996).
Burke et al., "Update on Alzheimer's Disease: Promising advances in Detection and Treatment," Postgraduate Medicine, 106(5) (1999).
Buxbaum et al., "Evidence That Tumor Necrosis Factor a Converting Enzyme is Involved in Regulated a-Secretase Cleavage of the Alzheimer Amyloid Protein Precursor," The Journal of Biological Chemistry, 273(43):27765-27767 (1998).
Caporaso et al., "Protein Phosphorylation Regulates Secretion of Alzheimer B/A4 Amyloid Precursor Protein," Proc. Natl. Acad. Sci. USA, 89:3055-3059 (Apr. 1992).
Carmeliet et al., "Growth properties and in vitro life span of Alzheimer disease and Down syndrome fibroblasts-a blind study", Mech. Aging Dev., vol. 53, pp. 17-33 (1990).
Chapman et al., "Genes, Models and Alzheimer's Disease," Trends in Genetics, 17(5) (May 2001).
Clark et al., "Evidence that the Bradykinin-induced Activation of Phospholipase D and of the Mitogen-activated Protein Kinase Cascade Involve Different Protein Kinase C. Isoforms," J. Biol. Chem. 270:7097-7103, 1995.
Connolly, G.P., "Fibroblast Models of Neurological Disorders: Fluorscence Measurement Studies", Trends Pharmacol. Sci. 19, 171-177 (1998).
Cornforth et al., "Automated Classification Reveals Morphological Factors Associated with Dementia," Applied Computing, 8:182-190 (2008).
Cruzblanca et al., "Bradykinin Inhibits M Current via Phospholipase C and Ca2+ Release from IP3-sensitive Ca1 + Stores in Rat Sympathetic Neurons, " Proc. Natl. Acad. Sci. USA, 95:7151-7156 (Jun. 1998).
Cuenda et al., "Use of Kinase Inhibitors to Dissect Signaling Pathways," Methods in Molecular Biology,vol. 99, Humana Press Inc., Totowa, NJ (2000).
Ekinci et al., "Hyperactivation of Mitogen-Activated Protein Kinase Increases Phospho-Tau Immunoreactivity Within Human Neuroblastoma: Additive and Synergistic Influence of Alteration of Additional Kinase Activities," Cell Mol. Neurobiol., 19(2):249-260 (1999).

El-Dahr et al., "Bradykinin Stimulates the ERKfwdanwElk-lfwdanwFos/AP-1 Pathway in Nesagial Cells." American Journal of Pyschology, 275(3 Part w):F343-F352 (Sep. 1998).
English-language Translation for JP 6-279311 dated Jun. 2008.
English-language Translation for JP10-90263 dated Apr. 10, 1998.
Est Profile Hs.400740, available at www.ncbi.nlm.nih.gov/UniGene, printed on Aug. 13, 2012, pp. 1-3.
Etchberrigaray et al., "Ionic and Signal Transduction Alterations in Alzheimer's Disease," Molecular Neurobiology, 20(1999).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Etcheberrigaray et al., "Calcium Responses in Fibroblasts from Asymptomatic Members of Alzheimer's Disease Families," Neurobiol. of Disease., 5:37-45 (1998).
Etcheberrigaray et al., "Potassium Channel Dysfunction in Fibroblasts Identifies Patients with Alzheimer Disease," Proc. Natl. Acad. Sci. USA, 90:8209-8213 (Sep. 1993).
Etcheberrigaray et al., "Therapeutic effects of PKC activators in Alzheimer's disease transgenic mice", PNAS, 01(30):11141-11146 (2004).
Etcheberrigary et al., "Molecular Mechanisms of Memory and the Pathophysiology of Alzheimer's Disease," Ann NY Acad Sci, 747:245-55 (1994).
European Search Report for EP 02 72 3236 dated Mar. 24, 2004.
Extended European Search Report issued on EP 08 02 0258 dated Jan. 30, 2009.
Extended European Search Report issued on EP 10 01 1288, dated Mar. 25, 2011.
Extended European Search Report issued on EP 10 01 1289 dated Mar. 23, 2011.
Extended European Search Report issued on EP 10 01 2836, dated Mar. 25, 2011.
Extended European Search Report issued on EP 10 011 290, dated Mar. 23, 2011.
Fan et al., "Arachidonic Acid and Related Methyl Ester Mediate Protein Kinase C Activation in Intact Platelets Through the Arachidonate Metabolism Pathways," Biochemical and Biophysical Research Communications, 169(3):933-940 (Jun. 29, 1990).
Favit et al., "Alzheimer's-specific effects of soluble β-amyloid on protein kinase C- and—degradation in human fybroblasts", Cell Biology, 95:5562-5567 (1998).
Favit et al., "KC Isoenzymes are Differentially Affected by Low Concentrations of Soluble Beta-Amyloid Protein in Alzheimer's Disease," Society for Neuroscience Abstracts, 23(1-2):293 (1993).
Final Office Action mailed Sep. 13, 2011, in U.S. Appl. No. 11/660,868.
Final Office Action mailed Oct. 11, 2011, in U.S. Appl. No. 12/083,056.
Frey et al. "Problems Associated with Biological Markers of Alzheimer's Disease," Neurochemical Research, 30(12):1501-1510 (Dec. 2005).
Furukawa et al., "Formation of Human Fibroblast Aggregates (Spheroids) by Rotational Culture", Cell Transplantation, vol. 10, pp. 441-445 (2001).
Gasparini et al., "Stimulaton β-Amyloid Precursor Trafficking by Insulin Reduces Intraneuronal βAmyloid and Requires Mitogen-Activated Protein Kinase Signaling," The Journal of Neuroscience, 21(8):2561-2570 (Apr. 15, 2001).
Gibson et al., "Calcium stores in cultured fibroblasts and their changes with Alzheimer's disease," Biochimica et Biophysica Acta, 1316:71-77 (1996).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Govoni et al., "Cytosol Protein Kinase C Downregulation in Fibroblasts from Alzheimer's Disease Patients," Neurology, 43:2581-2586 (1993).

(56) References Cited

OTHER PUBLICATIONS

Grant et al., "Phosphorylation of Mitogen-Activated Protein Kinase is Altered in Neuroectoderman Cells Overexpressing the Human Amyloid Precursor Protein 751 Isoform," Molecular Brain Research., 72:115-120 (1999).
Greenberg et al., "Secreted Beta-amyloid Precursor Protein Stimulated Mitogen-activated Protein Kinase and Enhances Tau Phosphorylation," Proc Natl Acad Sci USA, 91:7104-7108 (1994).
Growdon et al., "Biomarkers of Alzheimer Disease", Arch Neurol., vol. 56, No. 3, pp. 281-283, 1999.
Haug et al., "Decreased Inositol (1,4,5)-Trisphosphate Receptor Levels in Alzheimer's Disease Cerebral Cortex: Selectivity of Changes and Possible Correlation to Pathological Severity," Neurodegeneration, 5:169-176 (1996).
Hetman et al., "Role of Extracellular Signal Regulated Kinases 1 and 2 in Neuronal Survival," Eur. J. Biochem, 271:2050-2055 (2004).
Hirashima et al., "Calcium Responses in Human Fibroblasts: A Diagnostic Molecular Profile for Alzheimer's Disease," Neurology of Aging, 17(4):549-555 (1996).
Hogervorst et al., "The Validity and Reliability of 6 Sets of Clinical Criteria to Classify Alzheimer's Disease and Vascular Dementia in Cases confirmed Post-Mortem: Added Value of a Decision Tree Approach," Dement Geriatr Coqn Disord 2003:16:170-180.
Hongpaisan et al., "A structural basis for enhancement of long-term associative memory in single dendritic spines regulated by PKC", Proc. Natl. Acad. Sci. USA, vol. 104, No. 49, pp. 19571-19576, Dec. 4, 2007.
Huang et al., "Increased Inositol 1,4, 5-Trisphosphate Accumulation Correlates Withan Up-Regulation of Bradykinin Receptors in Alzheimer's Disease," Journal of Neurochemistry, 64(2):761-766 (Feb. 1995).
Huang et al., "Inositol Phosphates and Intracellular Calcium after Bradykinin Stilumation in Fibroblasts from Young, Normal Aged and Alzheimer Donors," Neurobiology of Aging, US, 12(5):469-473 (Sep. 1991).
Huynh et al., "Reduced Protein Kinase C Immunoreactivity and Altered Protein Phosphorylation in Alzheimer's Disease Fibroblasts," Arch Neurol 46 (1989).
Hyman et al.,, "Extracellular Signal-Regulated Kinase (MAP Kinase) Immunoreactivity in the Rhesus Monkey Brain." Neuroscience Letters, 166:113-116 (1994).
International Preliminary Report on Patentability and Written Opinion for PCT/2005/036014 dated Apr. 24, 2008.
International Preliminary Report on Patentability and Written Opinion for PCT/2006/022156 dated Apr. 24, 2008.
International Preliminary Report on Patentability and Written Opinion for PCT/US2006/037186 dated Apr. 16, 2008.
International Search Report and Written Opinion for PCT/US2006/037186 dated Apr. 11, 2007.
International Search Report and Written Opinion for PCT/US2009/051927 dated Jan. 28, 2011.
International Search Report and Written Opinion issued in PCT/US2010/051236 on Mar. 2, 2011.
International Search Report and Written Opinion on PCT/US2005/036014 dated Oct. 19, 2006.
International Search Report and Written Opinion on PCT/US2006/022156 dated Feb. 8, 2007.
International Search Report for PCT/US2004/38160 dated Nov. 4, 2005.
International Search Report issued on PCT/US2005/036014, published Apr. 19, 2007.
International Search Report issued on PCT/US2006/022156, published Apr. 19, 2007, 6 pages.
International Search Report issued on PCT/US2009/002120, dated Sep. 25, 2009.
Irizarry et al., "Biomarkers of Alzheimer Disease in Plasma," The Journal of the American Society for Experimental NeuroTherapeutics, 1:226-234 (Apr. 2004).
Ito et al., "Internal Ca2+ Mobilization is Altered in Fibroblasts from Patients with Alzheimer Disease." Proc Natl Acad Sci USA, 91:534-538 (1994).
Jin et al., "Changes in Protein Kinases in Brain Aging and Alzheimer's Disease," Drugs &Aging, 6(2):136-149 (1995).
Johnson et al., "IQGAP1 regulation and roles in cancer", Cellular Signalling, vol. 21, pp. 1471-1478 (2009).
Kanno et al., "The Linoleic Acid Derivative DCP-LA Selectively Activates PKC-ε, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ε", Dept. of Physiology, Hyogo College of Med., Hyogo, Japan, p. 552 (2006).
Khan et al., "A Cellular Model of Alzheimer's Disease Therapeutic Efficacy: PKC Activation Reverses a Beta-Induced Biomarker Abnormality on Cultured Fibroblasts," Neurobiology of Disease, 34(2): 332-339, vol. 34, No. 2 (May 2009).
Khan et al., "An Internally Controlled Perifpheral Biomarker for Alzheimer's Disease: Erkl and Erk2 responses to the Inflammatory Signal Bradykinin," PNAS, vol. 103, No. 35, pp. 13203-13207, Aug. 29, 2006.
Kilpatrick et al., "Regulation of TNF Mediated Antiapoptoptic Signaling in Human Neutrophils: Role of -PKC and ERK1/2," Journal of Leukocyte Biology, 80:1512-1521 (Dec. 2006).
Kleinman et al., "Use of extracellular matrix components for cell culture", Analytical Biochemistry, 166, pp. 1-13, (1987).
Kurumatani et al., "Loss of Inositol 1,4,5-trisphosphate Receptor Sites and Decreased PKC Levels Correlate with Staging of Alzheimer's Disease Neurofibrillary Pathology" Brain Research, 796:209-221 (1998).
Kuzirian et al., "Bryostatin Enhancement of Memory in Hermissenda", Biol. Bull. 210:201-214 (Jun. 2006).
Laporte et al., "Role of ERK MAP Kinases in Responses of Cultured Human Airway Smooth Muscles Cells to IL-1B." Am. J. Physiol. Lung Cell Mol. Physiol., 277:943-951 (1999).
Laurent-Matha et al., "Catalytically inactive human cathepsin D triggers fibroblast invasive growth", Journal of Cell Biology, vol. 168, No. 3, pp. 489-499, Jan. 31, 2005.
Leissring et al., "Capacitative Calcium Entry Deficits and Elevated Luminal Calcium Content in Mutant Presenilin-1 Knockin Mice," The Journal of Cell Biology, 149 (2000).
Leissring et al., "Presenilin-2 Mutations Modulate Amplitude and Kinetics of Inositol 1,4,5-Trisphosphate-mediated Calcium Signals," The Journal of Biological Chemistry, 274(46):32535-32538 (Nov. 12, 1999).
Lu et al., P44mpk MAP Kinase Induces Alzheimer Type Alterations in Tau Function and in Primary Hippocampal Neurons, J. Neurosci. Res., 35:439-444 (1993).
Luigi et al., "Inflammatory Markers in Alzheimer's Disease and Multi-Infarct Dementia," Mechanisms of Ageing and Development, 122:1985-1995 (2001).
Masliah et al., "Differential Involvement of Protein Kinase C Isozymes in Alzheimer's Disease," The Journal of Neuroscience,10:7, 2113-2124, Jul. 1990.
Masliah, "Protein Kinase C Alteration is an Early Biochemical Marker in Alzheimer's Disease," The Journal of Neuroscience, 11(9): 2759-2767 (1991).
Mattson et al., "Presenilin-1 Mutation Increases Neuronal Vulnerability to Focal Ischemia In Vivo and to Hypoxia and Glucose Deprivation in Cell Cuture: Involvement of Perturbed Calcium Homeostatis," The Journal of Neuroscience, 20(4):1358-1364 (Feb. 15, 2000).
Mattson, M. et al., "Presenilin Mutaitons and Calcium Signaling Defects in the Nervous and Immune Systems", BioEssays 23.8, 733-744 (2001).
McDonald et al., "β-Amyloid Fibrils Activate Parallel Mitogen-Activated Protein Kinase Pathways in Microglia and THP1 Monocytes," J Neurosci, 18:4451-4460 (1998).
Nagata et al., "FR236924, a Newly Synthesized Derivataive of Linoleic Acid, Ameliorates Memory Deficits in Rats Intraventricularly Injected with Amyloid-Beta Peptide," Jpn. J. Physiol. 53,Suppl. 2003(319): S261.

(56) References Cited

OTHER PUBLICATIONS

Nagata et al., "The Newly Synthesized Linoleic Acid Derivative CP-LA Ameliorates Memory Deficits in Animal Dmodels Treated with Amyloid-β Peptide and Scopolamine", Psychogeriatrics, 5:22-126 (2003).
Neve et al., "Alzheimer's Disease: Dysfunction of a Signalling Pathway Mediated by the Amyloid Precursor Protein?" Biochem. Soc. Symp. 67:37-50, (No Year Provided).
NME Digest, Drug News Perspect, 2002, pp. 666-674, vol. 15, No. 10.
Oddo et al., "Temporal Profile of Amyloid-β (AB) Oligomerization in an in Vivo Model of Alzheimer Disease—A Link Between AB and TAU Pathlogy," Journal of Biological Chemistry, 281(3):1599-1604 (Jan. 20, 2006).
Office Action (final) mailed Oct. 17, 2013, in U.S. Appl. No. 12/729,042.
Office Action (Restriction Requirement) mailed Dec. 2, 2010, in U.S. Appl. No. 12/083,056.
Office Action (Restriction Requirement) mailed May 23, 2011, in U.S. Appl. No. 12/510,681.
Office Action (Restriction Requirement) mailed Oct. 27, 2010, in U.S. Appl. No. 12/729,042.
Office Action mailed Aug. 24, 2012, in U.S. Appl. No. 12/083,056.
Office Action mailed Dec. 12, 2010, in U.S. Appl. No. 11/660,868.
Office Action mailed Oct. 11, 2012, in U.S. Appl. No. 12/896,862.
Office Action mailed Sep. 20, 2012, in U.S. Appl. No. 12/729,042.
Office Action (Requirement for Restriction) mailed Aug. 12, 2010, in U.S. Appl. No. 11/660,868.
Office Action mailed Apr. 29, 2011, in U.S. Appl. No. 12/083,056.
Office Action mailed Aug. 17, 2012, in U.S. Appl. No. 11/660,868.
Office Action mailed Jul. 31, 2013, in U.S. Appl. No. 13/401,459.
Office Action mailed Jun. 7, 2011, in U.S. Appl. No. 12/729,042.
Office Action mailed Nov. 15, 2012, in U.S. Appl. No. 12/510,707.
Ohta et al., "Stearic Acid Facilities Hoppocampal Neurotransmission by Enhancing Micotinic Ach Receptor Responses via an PKC Pathway," Molecular Brain Research, 119:83-89 (Aug. 27, 2003).
Pascale et al., "Enhanced BK-Induced Calcium Responsiveness in PC12 Cells Expressing the C100 Fragment of the Amyloid Precursor Protein," Brain Res Mol Brain Res, 72:205-2 (1999).
Pasinetti GM., "Use of cDNA Microarray in the Search for Molecular Markers Involved in the Onset of Alzheimer's Disease Dementia", J Neurosci Res., 65(6):471-476, Aug. 31, 2001.
Pub Chem Compound, XP002550143 (May 27, 2005).
Putney, Jr., "Presenilins, Alzheimer's Disease, and Capacitative Calcium Entry," Neuro, 27:411-412(2000).
Racchi et al., "Bradykinin-induced amyloid precursor protein secretion: a protein kinase C-independent mechanism that is not altered in fibroblasts from patients with sporadic Alzheimer's disease", Biochem J., vol. 330, pp. 1271-1275, 1998.
Rapoport et al., "PD98059 Prevents Neurite Degeneration Induced by Fibrillar B-Amyloid in Mature Hippocampal Neurons", J. Neurochem., vol. 74, pp. 125-133, 2000.
Reynolds et al., "Phosphorylation Sites on Tau Identified by Nanoelectrospray Mass Spectrometry:Differences In Vitro Between the Mitogen-Activated Protein Kinase ERK2, c-Jun N-Terminal Kinase and 0 P38, and Glycogen Synthase Kinase-3B,"0 J. Neurochem., 74:1587-1595 (2000).
Roux et al., "ERK and p38 MAPK-Activated Kinase Protein Kinases: a Family of Protein Kinase with Diverse Biological Functions," Microbiology and Molecular Biology Reviews, 68(2):320-344 (Jun. 2004).
Sato et al., "Elevated Amyloid Beta Protein (1-40) Level Induces CREB Phosphorylation at Serine-133 via p44/42 MAP kinase (Erk1/2)-dependent pathway in rat pheochromocytoma PC12 cells," Biochemical and Biophysical Research Communications, 232(3):637-642(Mar. 27, 1997).
Sheehan et al., "Calcium Homeostasis and Reactive Oxygen Species Production in Cells Transformed by Mitochondria from Individuals with Sporadic Alzheimer's Disease," The Journal of Neuroscience, 17(12):4612-4622 (Jun. 15, 1997).
Solerte et al., "Hemorheological Changes and Overproduction of Cytokines from Immune Cells in Mild to Moderate Dementia of the Alzheimer's Type: Adverse Effects on Cerebromicrovascular System," Neurobiology of Aging, 21(2):271-287 (2000).
Sun et al., "Poststroke neuronal rescue and synaptogenesis mediated in vivo by protein kinase C in adult brains", Proc. Natl. Acad. Sci. USA, Sep. 9, 2008; vol. 105, No. 36, pp. 13620-13625.
Sun et al., "Dual Effects of Bryostatin-1 on Spatial Memory and Depression", Eur. J. Pharmacol., vol. 512, pp. 43-51, 2005.
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters. 13:1037-1040 (2003).
Tanzi et al., "The Gene Defects Responsible for Familial Alzheimer's Disease," Neurobiology of Disease, 3:159-168 (1996).
Tesco et al., "Growth properties of familial Alzheimer skin fibroblasts during in vitro aging", Exp Gerontology, 28(1):51-8, 1993.
Thal et al., "The Role of Biomarkers in Clinical Trials for Alzheimer Disease," Alzheimer Dis Assoc Disord, 20(1) Jan.-Mar. 2006.
Urbanelli et al., "Cathepsin D expression is decreased in Alzheimer's disease fibroblasts", Neurobiology of Aging, vol. 29, pp. 12-22 (2008).
Weeraratna et al., "Alterations in Immunological and neurological gene expression patterns in Alzheimer's disease tissues", vol. 313, pp. 450-461 (2007).
Yaguchi et al.. "Effects of Cis-unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1)105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Yang et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Yoo et al., "Presenilin-Mediated Modulation of Capacltative Calcium Entry," Neuron, 27:561-572 (Sep. 2000).
Youdim et al., "Molecular Basis of Neuroprotective Activities of Rasagiline and the Anti-Alzheimer Drug TV3326 [(N-Propargyl-(3R)Aminoindan-5-YL)-Ethyl Methyl Carbamate]." Cellular and Molecular Neurobiology. 21(6): 555-573 (Dec. 2001).
Young, et al., "Decreased Brain [3H]inositol1 ,4,5-trisphosphate Binding in Alzheimer's Disease," Neuroscience Letters, 94:198-202 (2000).
Zhang et al., "Oxidative Stress Differentially Modulates Phosphorylation of ERK, p38 and CREB Induced by NGF or EGF in PC12 Cells." Neurobiology of Aging, 20:271-278 (1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Dysfunction of MAP Kinase signaling in Alzheimer's Disease," Society of Neuroscience, Abstracts 25, 31st Annual Meeting of the Society of Neuroscience: San Diego, CA, USA, 27(1):924, (Nov. 10-15, 2001).
Zhao et al., "Impairment of Phosphatase 2A Contributes to the Prolonged MAP Kinase Phosphorylation in Alzheimer's Disease Fibroblasts," Neurobiology of Disease, 14(3):458-469 (Dec. 2003).
Zhu et al., "The role of mitogenactivated protein kinase pathways in Alzheimer's disease," Neurosignals, 11(5):270-281, Sep. 2002.

* cited by examiner

STIMULUS-ELICITED GENOMIC PROFILE MARKERS OF ALZHEIMER'S DISEASE

This application claims the benefit of U.S. provisional application Ser. No. 61/084,154, filed on Jul. 28, 2008, the disclosure of which is incorporated herein by reference in its entirety.

FIELD OF THE INVENTION

The present invention relates to a method for diagnosing Alzheimer's disease using PKC-elicited gene expression profiles.

BACKGROUND OF THE INVENTION

Alzheimer's disease (AD) is a neurodegenerative disorder characterized by the progressive decline of memory and cognitive functions. Dementia associated with AD is referred to as senile dementia of the Alzheimer's type (SDAT) in usage with Alzheimer's disease. AD is characterized clinically by progressive loss of memory, cognition, reasoning, judgment, and emotional stability that gradually leads to profound mental deterioration and ultimately, death. Although there are many hypotheses for the possible mechanisms of AD, one central theory is that the excessive formation and accumulation of toxic beta-amyloid (Aβ) peptides either directly or indirectly affects a variety of cellular events and leads to neuronal damage and cell death (Selkoe, *Neuron*. 1991; 6(4): 487-98 1991; Selkoe, *J Clin Invest*. 2002; 110(10):1375-81).

AD is a progressive disorder with a mean duration of around 8-15 years between onset of clinical symptoms and death. AD is believed to represent the seventh most common medical cause of death and affects about 5 million people in the United States. The prevalence is expected to reach 7.7 million by 2030. About 1 in 8 people over the age of 65, 13% of this population, have AD (Alzheimer's Association 2008 Alzheimer's Disease Facts and Figures). AD currently affects about 15 million people world-wide (including all races and ethnic groups) and owing to the relative increase of elderly people in the population its prevalence is likely to increase over the next two to three decades. AD is at present incurable.

To date, there is limited opportunity for prophylactic intervention for AD because of insufficient diagnostic methods. At present, a definitive diagnosis of AD requires observing lesions in the brain tissue of patients post-mortem or, rarely, in small biopsied samples of brain tissue taken during an invasive neurosurgical procedure. Nevertheless, physicians routinely attempt to distinguish AD from other forms of dementia based on a battery of symptoms, relying on the known correlation between such symptoms and the lesions observed in biopsies. Tests currently used to diagnose AD include combinations of qualitative questionnaires such as the Mini-Mental State Examination (MMSE), the Mini-Cognitive Examination, and the AD Cooperative Study-Activities of Daily Living Scale (ADCS-ADL); physical and neurological evaluation; and structural (MRI, CT) and functional brain imaging (PET; FDG-PET). These tests are typically conducted to rule out other disease or conditions rather than to provide a definitive diagnosis of AD.

Some methods exist for detecting pathogenic biomarkers for AD, such as Aβ, Tau, and Neural thread protein/AD7C in living subjects. For example, detection of Aβ in a living subject include direct (imaging) or indirect (biochemical) detection. In vivo imaging of Aβ can be achieved using radio-iodinated flavone derivatives as imaging agents (Ono et al., *J Med Chem*. 2005; 48(23):7253-60) and with amyloid binding dyes such as putrescein conjugated to a 40-residue radioiodinated A peptide (yielding $^{125}$I-PUT-A 1-40). This agent was shown to cross the blood-brain barrier and bind to Aβ plaques (Wengenack et al., *Nature Biotechnology*. 2000; 18(8): 868-72). Imaging of Aβ also was shown using stilbene [$^{11}$C]SB-13 and the benzothiazole [$^{11}$C]6-OH-BTA-1 (also known as [$^{11}$C]PIB) (Nicholaas et al., *Am J Geriatr Psychiatry*. 2004; 12:584-595).

Quantitation of Aβ (1-40) in the peripheral blood also has been demonstrated using high-performance liquid chromatography coupled with tandem mass spectrometry in a linear ion trap (Du et al., *J Biomol Tech*. 2005; 16(4):356-63). Detection of single Aβ protein aggregates in the cerebrospinal fluid of Alzheimer's patients by fluorescence correlation spectroscopy also has been described (Pitschke et al., *Nature Medicine*. 1998; 4: 832-834). U.S. Pat. No. 5,593,846 describes a method for detecting soluble Aβ. Indirect detection of Aβ peptide and receptor for advanced glycation end products (RAGE) using antibodies also has been described. Lastly, biochemical detection of increased BACE-1 activity in cerebrospinal fluid using chromogenic substrates also has been postulated as diagnostic or prognostic indicator of AD (Verheijen et al., *Clin Chem*. 2006; 52:1168-1174). Other methods include detection of Tau, and Neural thread protein/AD7C in the cerebrospinal fluid.

In an attempt to improve treatment and diagnosis of AD, numerous gene-expression profiles have been generated to compare genes expressed in post-mortem brain tissue with those expressed normal brain tissue using various techniques including microarray laser capture microdissection (Loring et al., *DNA and Cell Biology*. 2001; 20(11): 683-95; Mufson et al., *Neurochem. Res*. 2003; 27(10): 1035-48; Dunckley et al., *Neurobiol Aging*. Oct. 1, 2005; Brooks et al., *Brain Res*. 2007; 1127(1):127-35; Liang et al., *Physiological Genomics*. 2008; 33:240-256; Liang et al., *Proc Natl Acad Sci USA*. Mar. 10, 2008); Some gene-expression profiles using peripheral tissues, such as lymphocytes or fibroblasts, also have been generated in an attempt to identify gene expression profiles associated with familial (inherited) AD or evaluate the effect of a potential treatment on differentially expressed genes (Nagasaka et al., *Proc. Natl. Acad. Sci. USA*. 2005; 102(41): 14854-14859).

Current diagnostic measures for AD include identification of a clinical core of early, progressive and significant episodic memory loss plus one or more abnormal biomarkers (biological indicators) characteristic of AD, including atrophy (wasting) of the temporal lobe as shown on MRI; abnormal Aβ protein concentrations in the cerebrospinal fluid; a specific pattern showing reduced glucose metabolism on PET scans of the brain; and a genetic mutation associated with within the immediate family.

Like the physical and mental examinations, the foregoing methods are not yet totally reliable or accurate for a diagnosis of Alzheimer's because the same gene patterns are found in other diseases or conditions. As a result, the costs of diagnosing AD are enormous because of the numerous tests and specialists involved and because the inability to diagnose Alzheimer's in early stages precludes patients and their families from adequately planning for the future, increasing costs for long-term care. In addition, estimates rates of misdiagnoses or no definitive diagnosis are in the range of 50-75%.

There remains a need for a simpler way to achieve more definitive diagnoses of AD that are less expensive and invasive, more accurate, and which can be used at an earlier stage for quicker intervention. Importantly, because the neurodegenerative process and substantial cell loss likely begins well before manifestation of the cognitive symptoms of AD, an effective diagnostic test that could more accurately diagnose AD, including early AD and even a pre-disposition to AD, would be invaluable.

DETAILED DESCRIPTION

Figure 1:
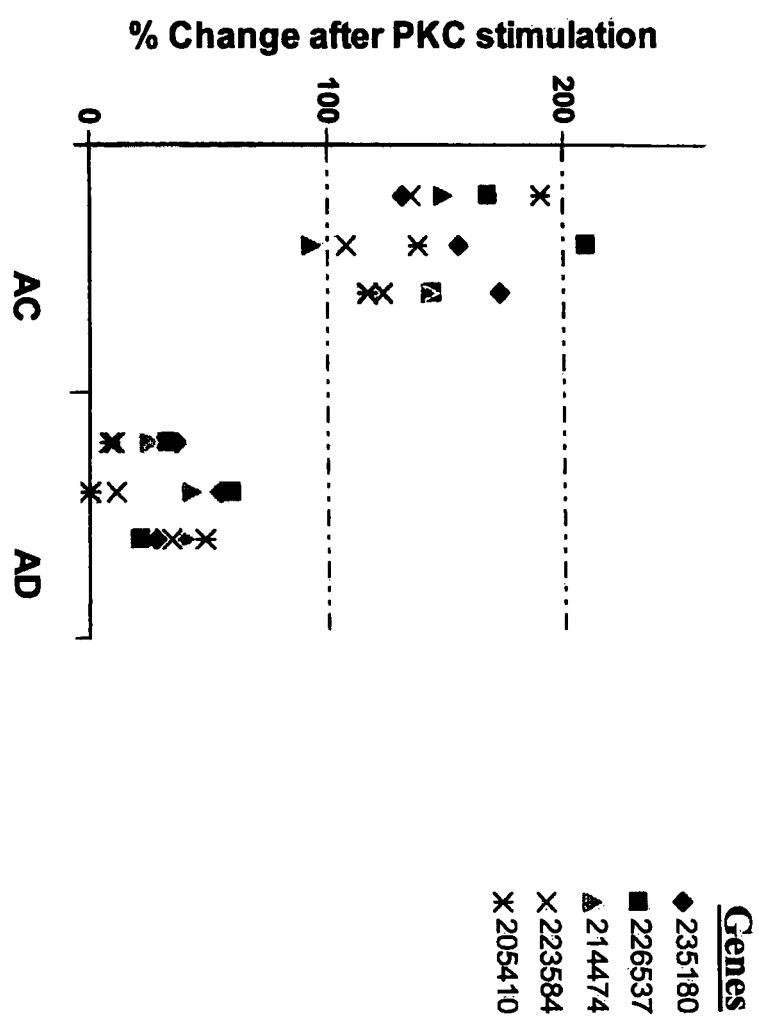
FIG. 1 depicts the decreased expression of certain genes in PKC-activated AD cells compared with PKC-activated control cells according to the method of the present invention.
Figure 2:
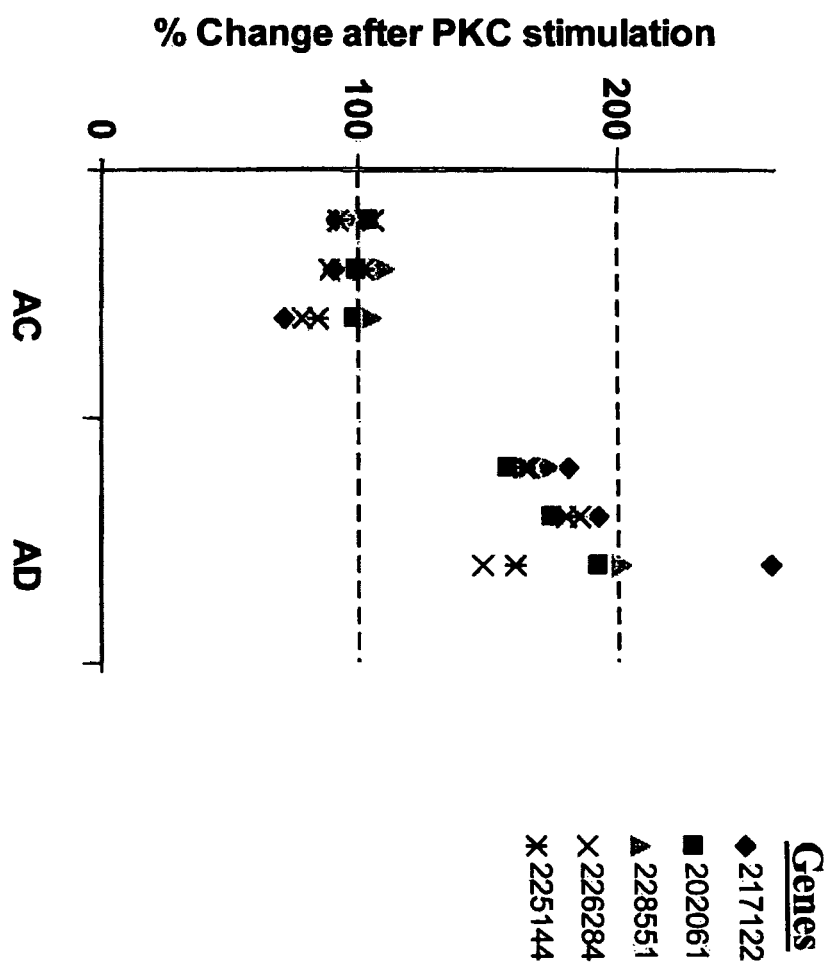
FIG. 2 depicts the increased expression of certain genes in PKC-activated AD cells compared with PKC-activated control cells according to the method of the present invention.

The invention provides methods for diagnosing Alzheimer's disease (AD). These methods are based upon detecting changes in gene expression following activation of protein kinase C (PKC). Protein kinase C (PKC) is one of the largest gene families of protein kinase (Liu and Heckman, *Cell Signal.* 1998; 10:529-542). Several PKC isozymes are expressed in the brain, including PKC, PKCβ1, PKCβ2, PKCδ, PKCε, and PKCγ. PKC is primarily a cytosolic protein, but with stimulation it translocates to the membrane. PKC has been shown to be involved in numerous biochemical processes relevant to Alzheimer's disease. Deficits of PKC isoforms have been found in AD brain tissue and in fibroblasts from AD patients. PKC also activates TNF-alpha converting enzyme (TACE), which is an enzyme that is involved in the proteolytic conversion of membrane-bound amyloid precursor protein (APP) to its non-pathogenic soluble form, known as soluble APP-alpha or sAPPalpha (Alkon et al., *Trends in Pharmacological Sciences.* 2007; 28(2): 51-60; Hurtado et al., *Neuropharmacology.* 2001; 40(8): 1094-1102). These sAPPα-producing enzymes are referred to generically as alpha-secretases. Activation of TACE by PKC also reduces cellular levels of pathogenic Aβ, which is produced by cleavage of APP by the beta-secretase enzyme (BACE). This is likely due to the fact that the TACE cleavage site is within the Aβ domain of APP. Overexpression of PKCε has been shown to selectively increased the activity of endothelin-converting enzyme, which degrades Aβ (Choi et al., *Proc. Natl. Acad. Sci. USA.* 2006; 103(21): 8215-8220). Moreover, studies have demonstrated that one PKC activator, bryostatin-1, reduces the levels of soluble Aβ and enhances recent memory (Etcheberrigaray et al., *Proc Natl Acad Sci USA.* 2004; 101(30): 11141-6; U.S. Pat. No. 6,825,229).

In addition, other studies have demonstrated that the translocated PKC can phosphorylate glutamate receptors, including NMDA receptors, as well as other proteins that are located in the postsynaptic density (Suzuki et al., *Brain Res.* 1993; 619:69-75). PKC has several impacts on NMDA receptors (MacDonald et al., *Curr Drug Targets.* 2001; 2:299-312). Specifically, PKC enhances the surface expression of NMDA receptors (Xiong et al., *Mol Pharmacol.* 1998; 54:1055-1063; Lan et al., *Nat Neurosci.* 2001; 4:382-390). Calcium flux through NMDA receptors is thought to play a critical role in synaptic plasticity, a cellular mechanism for learning and memory. One of the drugs approved to treat AD, memantine, binds to the NMDA receptor and inhibit the prolonged influx of calcium ions which forms the basis of neuronal excitotoxicity in AD.

Because the various PKC isozymes are involved in AD, the detection of Alzheimer's disease-specific differences in PKC-elicited gene expression and function in peripheral tissues provides the basis for highly practical and efficient tests for the early diagnosis of Alzheimer's disease, and provide a basis for identifying targets for therapeutic drug development.

DEFINITIONS

Protein Kinase C refers to any isoforms of PKC encoded by a PKC gene. The PKC gene family consists presently of 11 genes which are divided into four subgrounds: 1) classical PKCα (alpha), β1, β2 (beta) (β1 and β2 are alternatively spliced forms of the same gene) and γ (gamma), 2) novel PKCδ (delta), ε (epsilon), η (eta) and θ (theta), 3) atypical PKCξ (zeta), λ (lambda), η (eta) and ι (iota) and 4) PKCμ (mu). The α, β1, β2, and γ isoforms are calcium ion dependent, phospholipid and diacylglycerol-dependent and represent the classical isoforms of PKC, whereas the other isoforms are activated by phospholipid and diacylglycerol but are not dependent on calcium. All isoforms encompass 5 variable (V1-V5) regions, and the α, β1, β2, and γ isoforms contain four (C1-C4) structural domains which are highly conserved. All isoforms except PKC α, β1, β2, and γ lack the C2 domain, and the λ, η isoforms also lack nine of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme (House et al., *Science.* 1997; 238:1726-1728).

The term "Alzheimer's Disease" or "AD" refers to any condition where Aβ and/or neurofibrillary tangles eventually accumulates in the cells of the central nervous system, which accumulation that cannot be attributed to other disease or conditions such as CAA. AD may be heritable in a Familial manifestation, or may be sporadic. As used herein, AD includes Familial, Sporadic, as well as intermediates and subgroups thereof based on phenotypic manifestations. In addition, this term includes the development of Aβ in subjects having Down's Syndrome.

The term "Sporadic AD" refers to AD that develops later in life, usually after the age of about 65, and is not associated with a family history of AD or a mutation in a gene identified as being a risk factor for AD.

The term young-onset refers to AD that occurs in a person under age about 65. Young-onset includes but is not limited to Familial AD.

Familial AD refers to AD associated with inherited mutations in the presenilin-1 gene (PSEN-1), presenilin-2 gene (PSEN-2); the gene encoding Amyloid beta precursor protein (APP), and/or the gene encoding apolipoprotein E (APOE).

Early-stage AD refers to the stage of AD associated with moderate symptoms of cognitive decline such as memory loss or confusion. Memory loss or other cognitive deficits are noticeable, yet the person can compensate for them and continue to function independently. This stage correlates with Stage 4 of the Functional Assessment Staging (FAST) scale or mild AD according to the criteria defined in the Diagnostic and Statistical Manual of Mental disorders, 4th Edition (DSM-IV-TR) (published by the American Psychiatric Association), NINCDS-ADRDA, or MMSE.

Mild Cognitive Impairment (MCI) refers to a transition stage between the cognitive changes of normal aging and AD. A subject with MCI has cognitive impairments beyond that expected for their age and education, but that do not interfere significantly with their daily activities. A person with MCI may have impairments with memory, language, or another mental function. Not all subjects with MCI develop AD. As used herein, a subject with MCI is considered at risk for developing AD.

Other risk factors for AD are advancing age, mutations in PSEN-1, PSEN-2, APP and APOE, and As used herein, the term "subject" means a mammal. In one embodiment, the subject is a human.

The term "normal subject," as used herein, is relative to AD. That is, the subject does not exhibit AD, is not diagnosed with the specified disease, and is not at risk for developing the disease.

"Peripheral tissue" refers to a tissue that is not derived from neuroectoderm, and specifically includes olfactory epithelium, tongue, skin (including dermis and/or epidermis), and mucosal layers of the body.

The term "differentially expressed" or "differential expression" as used herein refers to a measurement of a cellular constituent varies in two samples, a control sample and a test sample. The cellular constituent can be either upregulated in the experiment relative to the control or downregulated in the experiment relative to the control sample.

As used herein, the phrase "detecting the level of expression" includes methods that quantitate expression levels as well as methods that determine whether a gene of interest is expressed at all. The detection can be qualitative or quantitative. In one specific embodiment, the differential expression is statistically significant.

As used herein, "upregulating" or "upregulation" means detecting an increased the amount or activity of a gene or gene product relative to a baseline or control state, through any mechanism including, but not limited to increased transcription, translation and/or increased stability of the transcript or protein product. Increased expression in a test cell includes a situation where the corresponding gene in a control cell is either unchanged by PKC activation or is downregulated in response to PKC activation.

As used herein, "down regulating" or "downregulation" refers to detecting a decrease in the amount or activity of a gene or gene product relative to a baseline or control state, through any mechanism including, but not limited to decreased transcription, translation and/or decreased stability of the transcript or protein product. Decreased expression in a test cell includes a situation where the corresponding gene in a control cell is either unchanged by PKC activation or is upregulated in response to PKC activation.

A "change in gene expression" refers to detection of upregulation or downregulation.

The term "microarray" or "nucleic acid microarray" refers to a substrate-bound collection of plural nucleic acids, hybridization to each of the plurality of bound nucleic acids being separately detectable. The substrate can be solid or porous, planar or non-planar, unitary or distributed. Microarrays or nucleic acid microarrays include all the devices so called in Schena (ed.), DNA Microarrays: A Practical Approach (Practical Approach Series), Oxford University Press (1999); *Nature Genet.* 21(1)(suppl.)1-60 (1999); Schena (ed.), Microarray Biochip: Tools and Technology, Eaton Publishing Company/BioTechniques Books Division (2000). These microarrays include substrate-bound collections of plural nucleic acids in which the plurality of nucleic acids are disposed on a plurality of beads, rather than on a unitary planar substrate, as is described, inter alia, in Brenner et al., *Proc. Natl. Acad. Sci. USA* 2000; 97(4):1665-1670.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

DESCRIPTION OF EMBODIMENTS

In one embodiment, the invention provides a method of diagnosing AD by detecting differences in the expression levels of genes in cells from a subject suspected of developing or having AD, in response to stimulation with a PKC activator ("test cells"), compared to expression of the same genes in normal control cells ("control cells") following stimulation with a PKC activator. In a specific embodiment, the control cells are derived age-matched control subjects and are stimulated with the same PKC activator as the test cells.

In another embodiment of the invention, increased gene expression in PKC-stimulated test cells compared to PKC-stimulated control cells (upregulation) indicates the presence of AD. In another aspect, decreased gene expression in stimulated test cells compared to PKC-stimulated control cells (downregulation) indicates the presence of AD. In a third aspect, absence of increased gene expression in stimulated test cells compared to PKC-stimulated control cells indicates the presence of AD. In a fourth aspect, absence of decreased expression in stimulated test cells compared to PKC-stimulated control cells indicates the presence of AD.

In another specific embodiment, the present invention provides a method for diagnosing early-stage AD by detecting the differential changes in gene expression. In specific embodiments, the method of the invention can be used to distinguish Alzheimer's pathology or dementia from that associated with other forms of dementia, such as frontotemporal degenerative dementias (e.g., Pick's disease, corticobasal ganglionic degenerations, and frontotemporal dementia), Huntington's disease, Creutzfeldt Jakob disease, Parkinson's disease, cerebrovascular disease, head trauma, and substance abuse.

In a further embodiment, the invention provides a method of evaluating disease progression by applying the methods to two or more samples from the same patient taken on separate occasions. This embodiment can also be used to evaluate the effect of any AD treatment administered after the first sample is taken but before the send sample is taken. Exemplary AD treatments that can be evaluated include Namenda® (memantine), Aricept® (donapazil) and Razadyne® (galantamine), an Exelon® (rivastigmine).

The present invention further provides a method of screening therapeutic substances for the treatment or prevention of AD by evaluating the effects of a test agent on the differential expression of genes according to the methods described herein.

In another embodiment, the present invention provides kits to carry out the diagnostic method of the present invention.

Table 1 provides the GenBank accession number for the genes identified to be down-regulated in the AD cells compared with the control cells. Table 2 provides the GenBank accession number for the genes identified to be upregulated in the AD cells compared with the control cells. Table 3 provides the specific genes and their relationship(s), and molecular biological and cellular functions.

In specific embodiments, the diagnostic method of the present invention comprises detecting differential expression in the control sample and the test sample of at least two genes listed in Table 1 or Table 2 in Example 1, below. In another specific embodiment, the diagnostic method of the present invention comprises detecting differential expression in the control sample and the test sample of at least five genes listed in Table 1 or Table 2. In a further specific embodiment, the diagnostic method of the present invention comprises detecting differential expression in the control sample and the test sample of at least ten genes listed in Table 1 or Table 2. In yet a further specific embodiment, the diagnostic method of the present invention comprises detecting differential expression in the control sample and the test sample of at least fifteen genes listed in Table 1 or Table 2. The specific genes and their relationship(s), molecular biological and cellular functions are described in Table 3.

Biological Samples

The present invention provides methods for the diagnosis of Alzheimer's disease using cells from subjects suspected of being at risk for developing AD or suspected of having AD. In the methods of the invention, the cells that are taken from the subject include any viable cells. In one embodiment, the cells are from peripheral tissues, i.e., non-neural tissue. In further specific embodiments, the tissue is skin, blood, mucosa, or cerebrospinal fluid.

In another specific embodiment, the cells are fibroblasts, epithethial cells, endothelial cells, or hematopoietic cells including lymphocytes. In a further specific embodiment, the cells are skin epithelial cells, skin fibroblast cells, blood cells or buccal mucosa cells. The cells may be fresh, cultured, or frozen prior to analysis. In a specific embodiment, a punch skin biopsy can be used to obtain skin fibroblasts from a subject. These fibroblasts are analyzed directly or introduced into cell culture conditions. In another specific embodiment, the cells are isolated from excised using laser capture microdissection to obtain a homogenous population of cells of the same type.

PKC Activators

The method of the present invention contemplates using any compound known to have the ability to activate PKC. PKC activators are known in the art and include bradykinin, phorbol esters such as phorbol 12-myristate 13-acetate (PMA), phorbol 12,13-dibutyrate (PDBu), phorbol 12,13-didecanoate (PDD), bombesin, cholecystokinin, thrombin, prostaglandin F2α and vasopressin. Other PKC activators include natural and unnatural diacylglycerols (DAG), including diacylglycerols with various fatty acids in the 1,2-sn configuration are active. In a specific embodiment, the DAG contains an unsaturated fatty acid. In one embodiment, the PKC activator is a macrocyclic lactone, including but not limited to those in bryostatin compound class and neristatin compound class. In another embodiment, the PKC activator is a benzolactam. In a further embodiment, the PKC activator is a pyrrolidinone. In a specific embodiment, the macrocyclic lactone is bryostatin. In a more specific embodiment, the bryostatin is bryostatin-1, -2, -3, -4, -5, -6, -7, -8, -9, -10, -11, -12, -13, -14, -15, -16, -17, or -18.

The present invention also contemplates diagnoses of AD by detecting changes in gene expression in cells contacted with PKC activators selective for a specific isoform or isoforms of PKC. For example, benzolactam activates PKC α, β and γ. Bryostatin-1 selectively activates PKCα. Bradykinin activates PKCα, -δ, and -ζ. PKCε and η have been showed to be activated upon the administration of nitric oxide donors such as diethylenetriamine/NO (DETA/NO) and S-nitroso-N-acetylpenicillamine (SNAP) diethylenetriamine/NO (DETA/NO) and S-nitroso-N acetylpenicillamine (SNAP) (Balafanova et al., *J. Biol. Chem.* 2002; 277(17): 15021-15027). More recently, polyunsaturated fatty acid derivatives have been shown to selectively activate PKCε.

Exemplary concentrations of PKC activators that can be used to stimulate cells according to the methods of the present invention at a range of about 0.01 nM to 100 μM, preferably, 0.5 nM to 10 μM, more preferably 1 nM to 1 μM, and most preferably 10 nM to 500 nM.

Gene Expression Profiling

Methods of evaluating changes in gene expression are well known in the art. The present invention contemplates both low-throughput methods such as Northern Blotting, in situ hybridization, and reverse transcription quantitative polymerase chain reaction (RVQ-PCR), and high-throughput methods such as microarrays and SAGE to detect differential gene expression. Preferably, detection is conducted using automatic, computerized equipment in a high-throughput setting, such as microarray technology. Such high-throughput equipment are commercially available, and techniques are well-known in the art.

In one specific embodiment, the method of the present invention provides detecting the gene transcript such as mRNA, including microRNA, cDNA or cRNA. The transcript can be from both coding and non-coding regions of the gene. The transcript can be detected in situ in the cell or in purified form extracted from the cell. In a specific embodiment, the nucleic acid is isolated and purified from the cell and then used in the gene expression assay.

In another embodiment, the method of the present invention provides detecting the protein product, or portion thereof, expressed from a gene transcript. Protein-based assays are also well-known in the art and include low-throughput methods such as Western blotting and ELISA, and high throughput protein microarrays.

In a further embodiment, the method of the present invention further comprises detecting the activity or activation state of the detected protein product, such as the phosphorylation of given protein.

In a specific embodiment of the invention, gene transcripts (e.g., cDNAs) from two different cells are hybridized to the binding sites of known gene transcripts on a microarray, one which is the test cell that has been stimulated with PKC activator and another the control cell, preferably of the same cell type, which has been stimulated with a PKC activator, preferably the same PKC activator. The nucleic acid derived from each of the two cell types are differently labeled so that they can be distinguished. Use of microarrays to evaluate differentially expressed transcripts are well known. See, e.g., U.S. Pat. No. 6,973,388. This technique typically involves preparing or purchasing microarrays containing known cDNA transcripts, extracting and labeling RNA from test cells, hybridizing the test RNA to the array, detecting and visualizing signal, performing statistical analysis on the results, and, optionally, validating the microarray results using low-throughput techniques.

Pre-made cDNA microarrays are commercially available from e.g., Affymetrix® (Santa Clara, Calif.), Agilent Technologies® (Santa Clara, Calif.) and AlphaGene® (Woburn, Mass.). These include whole genome arrays and targeted subsets of known genes.

In another specific embodiment, differential expression of genes is detected using serial analysis of gene expression (SAGE). SAGE quantitatively determines the amount of times a small portion of a specific mRNA transcript is expressed (a tag). The output of SAGE is a list of short sequence tags and the number of times it is observed. The major difference between microarray hybridization and serial analysis of gene expression (SAGE) techniques is that the latter does not require prior knowledge of the sequences to be analyzed; SAGE is a sequencing-based gene expression profiling technique.

In one embodiment of the invention, the test cells will demonstrate an observable difference in the level of expression of one or more genes compared with the level of expression of the same gene or genes in the control cells. In a specific embodiment, the differential expression is quantitative. In a further embodiment, the level gene expression detected in the test cells is about 1-fold, 2-fold, 5-fold, 10-fold and 100-fold upregulated or downregulated compared to the control cells.

Screening Methods for Therapeutics

In yet a further aspect, this invention relates to methods of screening therapeutic substances for the treatment or prevention of AD using the diagnostic tests described herein. According to this embodiment, compounds which reverse or improve the observed differences in gene expression described herein (i.e. back to or toward levels found in PKC-activated control cells) would be identified and selected as a substance potentially useful for the treatment or prevention of AD.

In one embodiment, the screening method comprises the steps of contacting cells from a subject that has been diagnosed with AD with a test compound for a period of time, followed by contacting the cells with an agent that is a PKC activator, and determining whether the test compound alters the differential expression of the genes identified according to the methods of the present invention towards levels observed in control cells from normal subjects.

In a specific embodiment, the cells contacted with the test compound are derived from a subject diagnosed with AD according to the methods of the present invention.

Kits

This invention also relates to kits comprising products useful for carrying out the diagnostic methods of the invention. The kits may also include instruments, buffers and storage containers necessary to perform one or more biopsies, such as punch skin biopsies. The kits can include high-density oligonucleotide arrays, reagents for use with the arrays, signal detection and array-processing instruments, gene expression databases and analysis and database management software. The kits may also contain instructions relating to the identification of differentially expressed genes used for the AD diagnosis.

As stated previously, the kits may contain a single diagnostic test or any combination of the tests described herein. All of the differences disclosed herein between control and AD cells form the basis for the clinical tests and diagnostic kits for AD disease diagnosis, as well as the methods of screening compounds for treatment or prevention of AD disclosed herein.

Combination Diagnostic Methods

It is contemplated that the diagnostic methods of the present invention may be used in combination with any other diagnostic methods. Exemplary methods include physical and neurological evaluation; biomarker detection; and structural (MRI, CT) and functional brain imaging (PET; FDG-PET).

As one example, the methods of the present invention can be used in combination with evaluating mutations in the genes known to be involved in Familial AD. Additional methods of diagnosing AD are described in U.S. Pat. Nos. 6,080,582 and 6,300,085 to Alkon et al., which methods detect the absence of potassium ion channels in the cells of an AD patient, differences in intracellular calcium ion concentration in AD and non-AD cells in response to potassium channel blockers specific for the potassium ion channel that is absent in the cells of an AD patient, and differences between AD and non-AD cells in response to activators of intracellular calcium release such as activators of inositol-1,4,5-trisphosphate (IP3). Additional diagnostic methods are described in application publication number WO2007/047029 to Alkon et al. directed to diagnosing AD in a subject by detecting alterations in the ratio of specific phosphorylated MAP kinase proteins (Erk1/Erk 2) in cells after stimulation with a PKC activator. See also, Zhao et al., *Neurobiol Dis*. October 2002; 11(1):166-83.

EXAMPLES

Example 1

Determination of Differentially-Expressed Genes in PKC-Activated AD Cells

This example describes the identification of differentially-expressed genes in AD cells according to the method of the present invention.

Materials and Methods

Bradykinin (BK; molecular weight, 1,060.2) was purchased from Calbiochem (San Diego, Calif.).

Skin Fibroblast Cell Culture.

Human skin fibroblast cell culture systems were used for these studies. Banked skin fibroblasts cells with the diagnoses AD and age-matched control from the Coriell Institute of Medical Research were cultured (supplemented with 10% serum and penicillin/streptomycin) at 37° C. with 5% $CO_2$ to the 90-100% confluence stage in 25-ml cell culture flasks. Cells were "starved" in serum-free medium (DMEM) for 24 h. A solution of 10 nM BK (in DMSO) was prepared in DMEM with 10% serum. Seven milliliters of the 10 nM BK solution was added to the culture flasks and incubated at 37° C. for 10 min. For the controls, the same amount of DMSO was added in DMEM with 10% serum. Seven milliliters of this medium with DMSO (<0.01%) was added to the culture flasks and incubated at 37° C. for 10 min. After washing four times with cold (4° C.) 1×PBS, flasks were kept in a dry ice/ethanol mixture for 15 min. Flasks were then removed from the dry ice/ethanol mixture, and the cells were treated with trypsin-EDTA (Invitrogen), centrifuged 400×g for 5 min, and the pellets were washed twice in PBS. The pellets were then quickly frozen in ethanol-$CO_2$ ice and transferred to −70° C.

Total RNA was then isolated from the cultured fibroblast pellets using an RNeasy mini kit (Qiagen, Hilden, Germany) according to the manufacturer's protocol, which typically a yield of 5-10 μg of RNA per $10^6$ cells. Nucleic acid was extracted from the cells according to standard procedures.

Microarray Analysis.

For microarray probing, reverse transcription, second-strand synthesis, and probe generation were performed according to the GeneChip Expression Analysis Technical Manual (Affymetrix, Santa Clara, Calif.). The generated probe was subjected to hybridization to oligonucleotide DNA chips, Human Genome U133A (Affymetrix). The arrays were scanned with a GeneArray Scanner (Hewlett-Packard).

Image Analysis and Data Quality Control. Scanner output image files were normalized and filtered by using MICROARRAY SUITE 5.0 software (Affymetrix). Normalization was performed by global scaling, with the arrays scaled to an arbitrary signal intensity value of 100. The detection metric (Presence or Absence calls) and decision of significant gene expression for a particular gene (probe set) was determined by using default parameters in the MICROARRAY SUITE 5.0 software.

Table 1 shows the genes down-regulated in AD cell lines following bradykinin stimulation but either activated or unchanged following bradykinin stimulation in age matched controls. Table 2 shows the genes up-regulated in AD cell lines following bradykinin stimulation but either down-regulated or unchanged following bradykinin stimulation in age matched controls. Table 3 provides the specific genes and their relationship(s), and molecular biological and cellular functions.

TABLE 1

Genes Down-regulated in AD

| Gene encoding | GenBank Accession No. | % CHANGE |
|---|---|---|
| *Homo sapiens* adaptor protein with pleckstrin homology and src homology 2 domains (APS), mRNA | NM_020979.1/DEF | 99 |
| *Homo sapiens*, KIAA1080 protein; Golgi-associated, gamma-adaptin ear containing, ARF-binding protein 2, clone MGC: 1002, mRNA, | BC000284.1/DEF | 64 |
| *Homo sapiens* sodium channel, voltage-gated, type I, beta polypeptide (SCN1B), mRNA. | NM_001037.1/DEF | 51 |
| *Homo sapiens* phosphoserine phosphatase-like (PSPHL), mRNA. | NM_003832.1/DEF | 77 |
| *Homo sapiens* hypothetical protein FLJ12455 (FLJ12455), mRNA. | NM_022078.1/DEF | 73 |
| Hs.50283 ESTs, Weakly similar to DUS8_HUMAN DUAL SPECIFICITY PROTEIN PHOSPHATASE 8 *H. sapiens* | AI492892 | 74 |
| Hs.112451 ESTs | T86629 | 76 |
| Hs.72325 Human DNA sequence from clone RP1-187J11 on chromosome 6q11.1-22.33. Contains the gene for a novel protein similar to *S. pombe* and *S. cerevisiae* predicted proteins, the gene for a novel protein similar to protein kinase C inhibitors, the 3 end of the gen | AW418666 | 79 |
| Hs.104613 RP42 homolog | AW468880 | 69 |
| *Homo sapiens* protein kinase, AMP-activated, beta 2 non-catalytic subunit (PRKAB2), mRNA. | NM_005399.1/DEF | 72 |
| Hs.294141 ESTs, Weakly similar to alternatively spliced product using exon 13A *H. sapiens* | BF433071 | 75 |
| *Homo sapiens* similar to CG9578 gene product (MGC3794), mRNA | NM_152902.1 | 61 |
| Hs.1742 IQ motif containing GTPase activating protein 1 | AI679073 | 88 |
| *Homo sapiens* paired mesoderm homeo box 1 (PMX1), transcript variant pmx-1a, mRNA. | NM_006902.2/DEF | 66 |
| Hs.20237 DKFZP566C134 protein | BF000166 | 85 |
| *Homo sapiens* ATPase, Ca++ transporting, plasma membrane 4 (ATP2B4), mRNA. | NM_001684.1/DEF = | 87 |
| Hs.127478 ESTs, Weakly similar to T32252 hypothetical protein T15B7.2 | AI813654 | 79 |
| Hs.50283 ESTs, Weakly similar to DUS8_HUMAN DUAL SPECIFICITY PROTEIN PHOSPHATASE 8 *H. sapiens* | AI492892 | 74 |

TABLE 2

Genes Up-regulated in AD

| Gene Encoding | GeneBank Accession No. | % CHANGE |
|---|---|---|
| Hs.69559 K1AA1096 protein | AW238632 | 46 |
| Hs.283732 ESTs | AW611729 | 97 |
| Hs.103189 lipopolysaccharide specific response-68 protein | AV740879 | 154 |
| Hs.6019 *Homo sapiens* cDNA: FLJ21288 fis, clone COL01927 | AA639752 | 475 |
| *Homo sapiens* full length insert cDNA clone | AP088033 | 74 |
| Hs.9977 ESTs | AW182938 | 155 |
| Hs.214646 KIAA0447 gene product | AL031282 | 150 |
| Hs.78893 KIAA0244 protein | BF430956 | 61 |
| Hs.42699 ESTs | AW956580 | 56 |
| Hs.3640 *Homo sapiens* mRNA | AI394529 | 60 |
| Hs.30957 *Homo sapiens* mRNA; cDNA DKFZp434E0626 | AL137364.1 | 86 |
| *Homo sapiens* forkhead box F2 (FOXF2), mRNA. | NM_001452.1 | 97 |
| K1AA1483 protein | BF111616 | 84 |
| Hs.28959 ESTs | AI457436 | 80 |
| *Homo sapiens* clone FBD3 Cri-du-chat critical region mRNA | AF056433 | 52 |
| *Homo sapiens* nuclear autoantigen (GS2NA), mRNA. / | NM_014574.1 | 71 |
| *Homo sapiens* Ste-20 related kinase (SPAK), mRNA. | NM_013233.1 | 46 |
| Hs.250646 baculoviral IAP | AI017106 | 285 |
| Hs.181300 sel-1 (suppressor of lin-12, *C. elegans*)-like | AI927770 | 75 |

TABLE 2-continued

Genes Up-regulated in AD

| Gene Encoding | GeneBank Accession No. | % CHANGE |
|---|---|---|
| Hs.5151 RAN binding protein 7 | BG291787 | 74 |
| EST SWlSNF related, matrix associated, actin dependent regulator of chromatin, subfamily a, member 3 | AI760760 | 56 |
| *Homo sapiens* eukaryotic translation initiation factor 4 gamma, 3 (EIF4G3), mRNA. | NM_003760.2/DEF | 68 |
| *Homo sapiens* chromosome condensation protein G (HCAP-G), mRNA. | NM_022346.1/DEF | 174 |
| Hs.293690 ESTs | AI816281 | 62 |
| *Homo sapiens* RBP1-like protein (BCAA), mRNA. | NM_016374.2/DEF | 68 |
| Hs.265644 ESTs | AW963328 | 74 |
| Hs.8895 ESTs | AA147933 | 63 |
| *Homo sapiens*, Similar to RIKEN cDNA 1700073K01 gene, clone MGC: 12458, mRNA | BC005357.1 | 63 |
| Hs.144477 hypothetical protein PRO2975/FL = gb: AF119911.1 | BG534245 | 55 |
| *Homo sapiens* mRNA for TGF-betaIIR alpha, complete cds. | D50683.1/DEF | 55 |
| *Homo sapiens* cDNA FLJ33255 fis, clone ASTRO2005553. | BU689502 | 105 |
| *Homo sapiens* ubiquitin specific protease 8 (USP8), mRNA. | NM_005154.1/DEF | 79 |
| Hs.79353 hypothetical protein FLJ13576 (TFDP1) | R60866 | 66 |
| Hs.79828 hypothetical protein FLJ20333 | A1823905 | 81 |
| *Homo sapiens* hypothetical protein FLJ10461 (FLJ10461), mRNA. | NM_018098.1/DEF | 45 |

TABLE 3

Specific subsets of genes and their biological, molecular and cellular functions.

| Gene Title | Gene Bank ID/Gene symbol | Biological processes | Molecular functions | Cellular components | Pathway |
|---|---|---|---|---|---|
| Transforming growth factor, beta receptor II (70/80 kDa) | D50683.1/DEF TGFBR2 | protein amino acid phosphorylation | nucleotide binding | membrane | TGF_Beta_Signaling_Pathway |
| | | transmembrane receptor protein serine/threonine kinase signaling pathway | magnesium ion binding | integral to membrane | |
| | | Positive regulation of cell proliferation | protein kinase activity | integral to membrane | |
| | | | protein serine/threonine kinase activity mransmembrane receptor protein serine/threonine kinase activity Receptor signaling protein serine/threonine kinase activity Receptor activity Transforming growth factor beta receptor activity Transforming growth factor beta receptor activity, type II Protein binding ATP binding Kinase activity Transferase activity Manganese ion binding metal ion binding | Receptor complex | |
| ATPase, Ca++ transporting, plasma membrane 4 | NM_001684.1/DEF ATP2B4 | transport | nucleotide binding | plasma membrane | |
| | | transport | magnesium ion binding | plasma membrane | |
| | | ion transport | catalytic activity | plasma membrane | |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| | | cation transport | calcium-transporting ATPase activity | integral to plasma membrane | |
| | | calcium ion transport | calcium-transporting ATPase activity | membrane | |
| | | metabolic process | calcium ion binding | integral to membrane | |
| | | | protein binding | | |
| | | | calmodulin binding | | |
| | | | ATP binding | | |
| | | | calcium ion transmembrane transporter activity | | |
| | | | ATPase activity, coupled to transmembrane movement of ions, phosphorylative mechanism | | |
| | | | hydrolase activity | | |
| | | | hydrolase activity, acting on acid anhydrides, catalyzing transmembrane movement of substances | | |
| | | | metal ion binding | | |
| phosphoserine phosphatase | NM_003832.1/ DEF PSPH | L-serine metabolic process | magnesium ion binding | | |
| | | L-serine biosynthetic process | catalytic activity | | |
| | | metabolic process | phosphoserine phosphatase activity | | |
| | | cell proliferation | phosphoserine phosphatase activity | | |
| | | | protein binding | | |
| | | amino acid biosynthetic process | | | |
| | | | hydrolase activity | | |
| | | | phosphoric monoester hydrolase activity | | |
| eukaryotic translation initiation factor 4 gamma, 3 | NM_003760.2/ DEF EIF4G3 | translation | RNA cap binding | eukaryotic translation initiation factor 4F complex | Translation_Factors |
| | | regulation of translation | RNA binding | | |
| | | regulation of translational initiation | translation initiation factor activity | | |
| | | regulation of translational initiation | binding | | |
| | | RNA metabolic process | protein binding | | |
| | | | protein binding | | |
| | | | translation factor activity, nucleic acid binding | | |
| epithelial cell transforming sequence 2 oncogene | NM_018098.1/ DEF ECT2 | intracellular signaling cascade | signal transducer activity | intracellular | |
| | | regulation of Rho protein signal transduction | guanyl-nucleotide exchange factor activity | | |
| | | positive regulation of I-kappaB kinase/NF-kappaB cascade | Rho guanyl-nucleotide exchange factor activity | | |
| | | | protein binding | | |
| BAT2 domain containing I | AW238632 BAT2DI | | | | |

TABLE 3-continued

Specific subsets of genes and their biological, molecular and cellular functions.

| Gene Title | Gene Bank ID/Gene symbol | Biological processes | Molecular functions | Cellular components | Pathway |
| --- | --- | --- | --- | --- | --- |
| helicase-like transcription factor | AI760760 EST HLTF | transcription regulation of transcription, DNA-dependent regulation of transcription from RNA polymerase II promoter chromatin modification | nucleotide binding nucleic acid binding DNA binding DNA binding RNA polymerase II transcription factor activity helicase activity protein binding ATP binding zinc ion binding transcription activator activity hydrolase activity ATPase activity metal ion binding | nucleus nucleus | |
| chromosome 14 open reading frame 43 | AV740879 C14orf43 | transcription regulation of transcription, DNA-dependent | DNA binding | nucleus | |
| similar to solute carrier family 35, member E2 | AL031282 RP11-345P4.4 | | | membrane integral to membrane | |
| paired related homeobox 1 | NM_006902.2/ DEF PRRXI | regulation of transcription, DNA-dependent multicellular organismal development regulation of transcription | DNA binding transcription factor activity transcription coactivator activity sequence-specific DNA binding | nucleus | |
| AT rich interactive domain 4B (RBP I-like) | NM_0I6374.2/ DEF ARID4B | chromatin assembly or disassembly transcription regulation of transcription, DNA-dependent | nucleic acid binding DNA binding chromatin binding | chromatin intracellular nucleus cytoplasm | |
| transcription factor Dp-1 | TFDP1 R60866 | S phase of mitotic cell cycle transcription regulation of transcription, DNA-dependent regulation of transcription from RNA polymerase II promoter apoptosis cell cycle cell proliferation epidermis development positive regulation of transcription, DNA-dependent | DNA binding transcription factor activity transcription factor activity transcription coactivator activity protein binding transcription activator activity | nucleus transcription factor complex | Cell_cycle_KEGG G1_to_S_cell_cycle_Reactome |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| striatin, calmodulin binding protein 3 | NM_014574.1 STRN3 | cell cycle | protein binding<br><br>calmodulin binding<br>calmodulin binding | membrane fraction<br>nucleus<br>cytoplasm<br>cytosol<br>membrane | |
| EF-hand calcium binding domain 2 | BC005357.1 EFCAB2 | | calcium ion binding | | |
| ubiquitin specific peptidase 8 | NM_005154.1/ DEF USP8 | DNA topological change<br>ubiquitin-dependent protein catabolic process<br>ubiquitin cycle<br><br>cell proliferation | double-stranded DNA binding<br><br>cysteine-type endopeptidase activity<br><br>ubiquitin thiolesterase activity<br>ubiquitin-specific protease activity<br>protein binding<br>protein binding<br>peptidase activity<br>cysteine-type peptidase activity<br>hydrolase activity | | |
| golgi associated, gamma adaptin ear containing, ARF binding protein 2 | BC000284.1/ DEF GGA2 | protein complex assembly<br>transport<br>intracellular protein transport<br>intracellular protein transport<br>protein transport<br><br>vesicle-mediated transport | protein binding<br><br>protein binding<br>protein transporter activity<br>ADP-ribosylation factor binding | intracellular<br><br>endosome<br>Golgi apparatus<br><br>trans-Golgi network<br>endosome membrane<br>membrane<br><br>membrane coat clathrin adaptor complex | |
| sodium channel, voltage-gated, type I, beta | NM_001037.1/ DEF SCN1B | transport<br><br>ion transport<br><br>sodium ion transport<br>sodium ion transport<br>synaptic transmission | ion channel activity<br><br>voltage-gated ion channel activity<br>voltage-gated sodium channel activity<br>sodium channel activity<br>sodium ion binding | membrane fraction<br>membrane<br><br>integral to membrane | |
| PHD finger protein 3 | BF430956 PHF3 | transcription<br>multicellular organismal development | protein binding<br>zinc ion binding<br><br>metal ion binding | | |
| IQ motif containing GTPase activating protein 1 | AI679073 IQGAP1 | signal transduction<br>signal transduction<br>small GTPase mediated signal transduction<br>regulation of small GTPase mediated signal transduction | GTPase inhibitor activity<br>GTPase activator activity<br>GTPase activator activity<br>Ras GTPase activator activity<br><br>protein binding<br>protein binding<br>protein binding<br>calmodulin binding<br>calmodulin binding | intracellular<br><br>cytoplasm<br><br>actin filament<br><br>plasma membrane<br><br>membrane | G13_Signaling_Pathway |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| serine threonine kinase 39 (STE20/SPS1 homolog, yeast) | NM_013233.1 STK39 | protein amino acid phosphorylation | nucleotide binding | membrane fraction | |
| | | protein amino acid phosphorylation | protein kinase activity | nucleus | |
| | | response to stress | protein serine/threonine kinase activity | nucleus | |
| | | | receptor signaling protein serine/threonine kinase activity | cytoplasm | |
| | | | protein-tyrosine kinase activity | cytoplasm | |
| | | | protein binding | basolateral plasma membrane | |
| | | | ATP binding | apical plasma membrane | |
| | | | ATP binding kinase activity transferase activity | | |
| DCN1, defective in cullin neddylation 1, domain containing I (S. cerevisiae) | AW468880 DOUN1D1 | | | | |
| protein kinase, AMP-activated, beta 2 non-catalytic subunit | NM_005399.1/ (DEF PRKAB2 | fatty acid biosynthetic process | protein binding | cAMP-dependent protein kinase complex | Fatty_Acid_Synthesis |
| | | signal transduction | kinase activity | AMP-activated protein kinase complex | |
| | | lipid biosynthetic process | protein kinase binding | | |
| histidine triad nucleotide binding protein 3 | AW418666 HINT3 | | catalytic activity | | |
| TIP41, TOR signaling pathway regulator-like (S. cerevisiae) | NM_152902.1 TIPRL | | protein binding | | |
| serine/threonine/ tyrosine interacting protein | AI492892 LOC730432 | protein amino acid dephosphorylation | phosphoprotein phosphatase activity | | |
| similar to serine/threonine/ tyrosine interacting protein | AI492892 STYX | dephosphorylation | protein tyrosine/serine/threonine phosphatase activity | | |
| | | | hydrolase activity phosphoric monoester hydrolase activity | | |
| baculoviral IAP repeat-containing 6 (apollon) | AI017106 BIRC6 | ubiquitin cycle | ubiquitin-protein ligase activity | intracellular | |
| | | apoptosis | endopeptidase inhibitor activity | membrane fraction | |
| | | anti-apoptosis | cysteine protease inhibitor activity | | |
| | | anti-apoptosis positive regulation of cell proliferation post-translational protein modification regulation of | ligase activity small conjugating protein ligase activity | | |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| | | protein metabolic process | | | |
| protein tyrosine phosphatase-like (proline instead of catalytic arginine), member b | AI813654 PTPLB | | protein binding | | |
| bone morphogenetic protein receptor, type II (serine/threonine kinase) | AI457436 BMPR2 | skeletal development | nucleotide binding | integral to plasma membrane | |
| | | protein amino acid phosphorylation | magnesium ion binding | membrane | |
| | | transmembrane receptor protein serine/threonine kinase signaling pathway | protein kinase activity | integral to membrane | |
| | | transmembrane receptor protein serine/threonine kinase signaling pathway | protein serine/threonine kinase activity | | |
| | | regulation of cell proliferation | transmembrane receptor protein serine/threonine kinase activity | | |
| | | | receptor signaling protein serine/threonine kinase activity | | |
| | | | receptor activity | | |
| | | | transforming growth factor beta receptor activity | | |
| | | | protein binding | | |
| | | | protein binding | | |
| | | | ATP binding | | |
| | | | kinase activity | | |
| | | | transferase activity | | |
| | | | manganese ion binding | | |
| | | | metal ion binding | | |
| zinc finger and BTB domain containing 2 | BF111616 ZBTB2 | transcription regulation of transcription, DNA-dependent | nucleic acid binding DNA binding | intracellular nucleus | |
| | | | protein binding zinc ion binding metal ion binding | | |
| KIAA1333 | AI823905 KIAA1333 | protein modification process | ubiquitin-protein ligase activity | intracellular | |
| | | ubiquitin cycle | protein binding | nucleus | |
| | | | protein binding zinc ion binding ligase activity metal ion binding | cytoplasm | |
| kelch repeat and BTB (POZ) domain containing 2 | BF000166 KBTBD2 | | protein binding | | |
| forkhead box F2 | NM_001452.1 FOXF2 | transcription regulation of transcription, DNA-dependent | DNA binding DNA binding | nucleus nucleus | |
| | | transcription from RNA polymerase II promoter | transcription factor activity | nucleus | |
| | | extracellular matrix | transcription factor activity | transcription factor complex | |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| | | organization and biogenesis | | | |
| | | establishment of polarity of embryonic epithelium | RNA polymerase II transcription factor activity | | |
| | | negative regulation of transcription, DNA-dependent | transcription coactivator activity | | |
| | | positive regulation of transcription, DNA-dependent | transcription activator activity | | |
| | | embryonic gut development | sequence-specific DNA binding sequence-specific DNA binding | | |
| G patch domain containing 3 | NM_022078.1/ DEF GPATCH3 | | nucleic acid binding | intracellular | |
| SH2B adaptor protein 2 | NM_020979.1/ DEF SH2B2 | B-1 B cell homeostasis | signal transducer activity | stress fiber | |
| | | signal transduction | transmembrane receptor protein tyrosine kinase adaptor protein activity | ruffle | |
| | | intracellular signaling cascade | SH3/SH2 adaptor activity | cytoplasm | |
| | | intracellular signaling cascade | SH3/SH2 adaptor activity | cytoplasm | |
| | | insulin receptor signaling pathway | protein binding | actin filament | |
| | | cytokine and chemokine mediated signaling pathway | JAK pathway signal transduction adaptor activity | plasma membrane | |
| | | regulation of metabolic process | | plasma membrane | |
| | | actin cytoskeleton organization and biogenesis | | membrane | |
| | | regulation of immune response | | | |
| | | antigen receptor-mediated signaling pathway | | | |
| non-SMC condensin I complex, subunit G | NM_022346.1/ DEF NCAPG | cell cycle mitosis mitotic chromosome condensation mitotic chromosome condensation cell division | binding protein binding | nucleus nucleus cytoplasm | |
| sel-1 suppressor of lin-12-like (*C. elegans*) | AI927770 SEL1L | Notch signaling pathway | binding | endoplasmic reticulum endoplasmic reticulum membrane membrane integral to | |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| | | | | membrane integral to membrane | |
| casein kinase 1, alpha 1 | BG534245 CSNK1A1 | protein amino acid phosphorylation protein amino acid phosphorylation Wnt receptor signaling pathway | nucleotide binding<br><br>protein serine/threonine kinase activity casein kinase I activity<br><br>ATP binding transferase activity | cytoplasm | |
| myeloid/lymphoid or mixed-lineage leukemia 2 | AI394529 MLL2 | in utero embryonic development transcription regulation of transcription, DNA-dependent regulation of transcription, DNA-dependent | DNA binding<br><br>DNA binding protein binding<br><br>protein binding<br><br>zinc ion binding metal ion binding | nucleus<br><br>nucleus histone methyltransferase complex | |
| hypothetical protein MGC24039 | AL137364.1 MGC24039 | | | | |
| CDNA FLJ30652 fis, clone DFNES2000011 | T86629 - | | | | |
| CDNA FLJ33255 fis, clone ASTRO2005553 | BU689502 - | | | | |
| Importin 7 | BG291787 1PO7 | protein import into nucleus, docking transport intracellular protein transport signal transduction protein transport | small GTPase regulator activity<br><br>transporter activity binding<br><br>protein binding<br><br>protein binding Ran GTPase binding protein transporter activity histone binding | soluble fraction<br><br>nucleus nuclear pore<br><br>nuclear pore<br><br>cytoplasm | |
| CDNA FLJ31066 fis, clone HSYRA2001153 | AA147933 - | | | | |
| Cri-du-chat region mRNA, clone NIBB11 | AF056433 - | | | | |
| | AF088033 - | ubiquitin cycle<br><br>ubiquitin cycle | ubiquitin-specific protease activity ubiquitin-specific protease activity peptidase activity cysteine-type peptidase activity hydrolase activity | cytoplasm<br><br>endoplasmic reticulum Golgi apparatus | |
| CDNA FLJ42233 fis, clone THYMU3000420 | AI816281 - | | | | |
| Thrombospondin 1 | AW956580 THBS1 | cell motility<br><br>cell adhesion | endopeptidase inhibitor activity signal transducer activity | extracellular region extracellular region | Inflammatory_Response_Pathway<br><br>TGF_Beta_Signaling_Pathway |

TABLE 3-continued

Specific subsets of genes and their biological, molecular and cellular functions.

| Gene Title | Gene Bank ID/Gene symbol | Biological processes | Molecular functions | Cellular components | Pathway |
|---|---|---|---|---|---|
| | | multicellular organismal development | structural molecule activity | | |
| | | nervous system development | calcium ion binding | | |
| | | blood coagulation | protein binding | | |
| | | | heparin binding | | |
| hypothetical protein LOC144871 | AA639752 LOC144871 | | | | |
| vacuolar protein sorting 41 homolog (S. cerevisiae) | AW963328 VPS41 | transport intracellular protein transport protein transport vesicle-mediated transport | binding protein binding zinc ion binding metal ion binding | | |
| Transcribed locus, moderately similar to XP_222679.3 PREDICTED: similar to FRBZ1 protein (FRBZI) [Rattus norvegicus] | BF433071 - | | | | |
| ESTs | AW611729 | unknown | Moderately similar to ALU_HUMAN ALU subfamily | unknown | |
| ESTs | AW182938 | unknown | | unknown | |

The foregoing demonstrates that PKC-activation elicits different genomic profiles in AD cells, as compared with control cells, which can be used to diagnose AD and individuals at risk for developing AD.

Patents, patent applications, publications, product descriptions, and protocols are cited throughout this application, the disclosures of which are incorporated herein by reference in their entireties for all purposes.

What is claimed:

1. A method of diagnosing Alzheimer's disease, said method comprising the steps of:
    i) contacting a population of test cells obtained from a subject suspected of having Alzheimer's disease with an agent that is a protein kinase C activator, wherein the protein kinase C activator is chosen from bradykinin, bryostatin, bombesin, cholecystokinin, thrombin, prostaglandin F2-alpha, and vasopressin; and
    ii) detecting changes in gene expression of at least two genes in the test cells when compared to gene expression of the at least two genes in non-Alzheimer's disease control cells contacted with a protein kinase C activator, wherein a decrease in the gene expression of the at least two genes in the test cells compared to the gene expression of the at least two genes in the control cells indicates that the individual has Alzheimer's disease,
    wherein the at least two genes are chosen from SH2B2 (SH2B adaptor protein 2, NM_020979.1); GGA2 (golgi associated, gamma adaptin ear containing, ARF binding protein 2, BC000284.1); SCN1B (sodium channel, voltagegated, type I, beta, NM_001037.1); PSPH (phosphoserine phosphatase, NM_003832.1); GPATCH3 (G patch domain containing 3, NM_022078.1); LOC730432 (serine/threonine/tyrosine interacting protein, AI492892); cDNA FLJ30652 fis, clone DFNES2000011 (T86629); HINT3 (histidine triad nucleotide binding protein 3, AW418666); DCUN1D1 (DCN1, defective in cullin neddylation 1, domain containing 1, AW468880); PRKAB2 (protein kinase, AMP-activated, beta 2 non-catalytic subunit, NM_005399.1); transcribed locus (similar to FRBZ1 protein (FRBZ1), BF433071); TIPRL (TIP41, TOR signaling pathway regulator-like, NM_152902.1); IQGAP1 (IQ motif containing GTPase activating protein 1, AI679073); PRRX1 (paired related homeobox 1, NM_006902.2); KBTBD2 (kelch repeat and BTB (POZ) domain containing 2, BF000166); ATP2B4 (ATPase, calcium transporting, plasma membrane 4, NM_001684.1); PTPLB (protein tyrosine phosphatase-like (proline instead of catalytic arginine), member b, AI813654), STYX (similar to serine/threonine/tyrosine interacting protein, AI492892), homologs thereof, and combinations thereof.

2. The method of claim 1, wherein the test cells are peripheral cells.

3. The method of claim 2, wherein the test cells are chosen from skin cells, blood cells, buccal mucosal cells, and cells from cerebrospinal fluid.

4. The method of claim 2, wherein the test cells are fibroblast cells or epithelial cells.

5. The method of claim 1, wherein the change in gene expression is measured using a microarray.

6. The method of claim 5, wherein the microarray is nucleic acid array wherein the nucleic acids are derived from the test and control cells.

7. The method of claim 6, wherein the nucleic acid is cDNA.

8. The method of claim 1, wherein the change in gene expression is measured using polymerase chain reaction.

9. The method of claim 8, wherein the polymerase chain reaction is real-time polymerase chain reaction.

10. The method of claim 1, wherein the protein kinase C activator that contacts the test cells and the protein kinase C activator that contacts the control cells are the same.

11. A method of diagnosing Alzheimer's disease, said method comprising the steps of:
   i) contacting a population of test cells obtained from a subject suspected of having Alzheimer's disease with an agent that is a protein kinase C activator, wherein the protein kinase C activator is chosen from bradykinin, bryostatin, bombesin, cholecystokinin, thrombin, prostaglandin F2-alpha, and vasopressin; and
   ii) detecting changes in gene expression of at least two genes in the test cells when compared to gene expression of the at least two genes in non-Alzheimer's disease control cells contacted with a protein kinase C activator, wherein a change in the gene expression is chosen from an increase of one or more genes of the at least two genes in the test cells compared to the gene expression of the one or more genes in the control cells, and a decrease in the gene expression of another one or more genes of the at least two genes in the test cells compared to the gene expression of the another one or more genes in the control cells indicates that the individual has Alzheimer's disease, wherein the increase of one or more genes are chosen from C14orf43 (lipopolysaccharide specific response protein-68; AV7480789), PHF3 (PHD finger protein 3; BF430956), STRN3 (striatin-binding protein 3; NM_014574.1), STK39 (serine threonine kinase STRN3 (striatin-binding protein 3; NM_014574.1), STK39 (serine threonine kinase 39, SPAK, NM_013233.1); 1P07 (Ran binding protein 7; importin 7, BG291787); HLTF (helicase-like transcription factor; AI760760); EIF4G3 (Eukaryotic translation initiation factor 4, gamma 3; NM_003760.2): NCAPG (Non-SMC condensin 1 complex, subunit G; NM_022346.1), TGFBR2 (TGF-β Receptor Type II D50683.1); USP8 (Ubiquitin specific peptidase-8, NM_005154.1); BAT2DI (BAT2 domain containing 1 helicase-like transcription factor; AW238632); LOC144871 (hypothetical protein LOC144871, AA639752); homo sapiens full length insert cDNA clone (ubiquitin cycle protein, AF088033); RP11-345P4.4 (similar to solute carrier 35, memmber E2, AL03128); THBS1(Thrombospondin 1, AW956580); MLL2 (myeloid/lymphoid or mixed-lineage leukemia 2; A139452); MGC24039 (hypothetical protein MGC24039, AL137364.1); FOXF2 (forkhead box F2, NM_001452.1); ZBTB2 (zinc finger and BTB domain containing 2, BF111616); BMPR2 (bone morphogenetic protein receptor, type II, A1457436); Cri-du-chat region mRNA (cone NIBB11, AF056433); BIRC6 (baculoviral IAP repeat-containing 6, apollon, AI017106): SEL1L (sel-1 suppressor of lin-12-like, AI927770); cDNA FLJ42233 fis, clone THYMU3000420 (A1816281); ARID4B (At rich interactive domain 4B (RBPI-like), NM_016374.2); VPS41 (vacuolar protein sorting 41 homolog, AW963328); cDNA FLJ31066 fis, clone HSYRA2001153 (AA147933); EFCAB2 (EF-hand calcium binding domain 2, BC005357.1); CSNK1A1 (casein kinase 1, alpha 1, BG534245); cDNA FLJ33255 fis, clone ASTRO2005553 (BU689502); KIAA1333 (ubiquitin cycle protein, A1823905); ECT2 (epithelial cell transforming sequence 2 oncogene; NM_018098.1); TFDP1 (transcription factor Dp-1, R60866); ESTs (AW611729); and ESTs (AW182938); homologs thereof, and combinations thereof; and wherein the decrease of another one or more genes are chosen from SH2B2 (SH2B adaptor for protein 2, NM_020979.1); GGA2 (golgi associated, gamma adaptin ear containing, ARF binding protein 2, BC000284.1); SCN1B (sodium channel, voltage-gated, type I, beta, NM_001037.1); PSPH (phosphoserine phosphatase, NM_003832.1); GPATCH3 (G patch domain containing 3, NM_022078.1); LOC730432 (serine/threonine/tyrosine interacting protein A1492892); cDNA FLJ30652 fis, clone DFNES2000011 (T86629); HINT3 (histidine triad nucleotide binding protein 3, AW418666); DCUN1D1 (DCN1, defective in cullin neddylation 1, domain containing 1, AW468880); PRKAB2 (protein kinase, AMP-activated, beta 2 non-catalytic subunit, NM_005399.1); transcribed locus (similar to FRBZ1 protein (FRBZ1), BF433071); TIPRL (TIP41, TOR signaling pathway regulatorlike, NM_152902.1); IQGAP1 (IQ motif containing GTPase activating protein 1, A1679073); PRRX1 (paired related homeobox 1, NM_006902.2); KBTBD2 (kelch repeat and BTB (POZ) domain containing 2, BF000166); ATP2B4 (ATPase, calcium transporting, plasma membrane 4, NM_001684.1); PTPLB (protein tyrosine phosphatase-like (proline instead of catalytic arginine), member b, A1813654); STYX (similar to serine/threonine/tyrosine interacting protein, A1492892); homologs thereof, and combinations thereof.

12. The method of claim 11, wherein the protein kinase C activator that contacts the test cells and the protein kinase C activator that contacts the control cells are the same.

* * * * *

UNITED STATES PATENT AND TRADEMARK OFFICE
CERTIFICATE OF CORRECTION

PATENT NO. : 8,822,166 B2  
APPLICATION NO. : 12/510707  
DATED : September 2, 2014  
INVENTOR(S) : Alkon et al.

Page 1 of 1

It is certified that error appears in the above-identified patent and that said Letters Patent is hereby corrected as shown below:

In the Claims

Claim 11, col. 31, line 33, "AV7480789)," should read -- AV740879 --.

Claim 11, col. 31, lines 49-50, "(similar to solute carrier 35, memmber E2, AL03128)" should read -- "(similar to solute carrier family 35, member E2, AL031282) --.

Claim 11, col. 31, line 52, "A139452)" should read -- A1394529) --.

Claim 11, col. 32, line 8, "(At rich interactive domain" should read -- (AT rich interactive domain --.

Signed and Sealed this
Twenty-seventh Day of January, 2015

Michelle K. Lee
*Deputy Director of the United States Patent and Trademark Office*